United States Patent [19]

Perdue

[11] Patent Number: 4,848,327
[45] Date of Patent: Jul. 18, 1989

[54] APPARATUS AND PROCEDURE FOR BLIND ALIGNMENT OF FASTENERS EXTENDED THROUGH TRANSVERSE HOLES IN AN ORTHOPEDIC LOCKING NAIL

[76] Inventor: Kevin D. Perdue, R.R. #4, P.O. Box 200, Sayre, Okla. 73662

[21] Appl. No.: 197,216

[22] Filed: May 23, 1988

[51] Int. Cl.$^4$ .......................... A61F 5/04; A61B 6/08; B23B 47/28; B23B 49/02
[52] U.S. Cl. ........................... 128/92 R; 128/92 VD; 128/92 YY; 128/316; 378/205; 408/91; 408/108; 408/115 B
[58] Field of Search ............. 128/92 VD, 92 R, 92 Z, 128/92 Y, 92 YZ, 92 YE, 305.1, 310, 316; 378/162, 163, 205; 408/72 R, 72 B, 81, 83, 87, 91, 103, 108, 115 R, 115 B

[56] References Cited

U.S. PATENT DOCUMENTS

| | | |
|---|---|---|
| 3,670,724 | 6/1972 | Bosacco . |
| 3,782,373 | 1/1974 | Smythe . |
| 3,814,089 | 6/1974 | Deyerle . |
| 4,257,411 | 3/1981 | Cho . |
| 4,281,649 | 8/1981 | Derweduwen . |
| 4,292,964 | 10/1981 | Ulrich . |
| 4,418,422 | 11/1983 | Richter et al. ...................... 378/205 |
| 4,541,424 | 9/1985 | Grosse et al. . |
| 4,549,538 | 10/1985 | Schadrack, III et al. . |
| 4,570,624 | 2/1986 | Wu . |
| 4,625,718 | 12/1986 | Olerud et al. . |
| 4,667,664 | 5/1987 | Taylor et al. . |
| 4,708,139 | 11/1987 | Dunbar, IV ................ 408/115 R X |

Primary Examiner—Richard J. Apley
Assistant Examiner—David J. Bender
Attorney, Agent, or Firm—Laney, Dougherty, Hessin & Beavers

[57] ABSTRACT

A method for placing screws in an orthopedic nail used in setting fractures of the long bones of the body. A fluoroscope assembly is used initially to develop an image on a monitor. This image enables the physician to adjust the fluoroscope assembly until the x-rays from the fluoroscope are propagated along lines which are coaxially aligned with the nail screw holes. This status of alignment is then used to allow reference marks to be made on the skin located on one or more lines projected through the limb containing the fractured bone in coaxial alignment with the nail screw holes.

The limb is then incised at the location of one or more of these alignment marks allowing tubular drill guides of a jig to be set against the bone in a position of coaxial alignment with the screws holes through the nail. Before using the drill guides of the jig to drill holes in the bone, precise coaxial alignment of the drill guides with the screw holes through the nail is obtained by utilizing as a part of the jig, and in fixed relation to each drill guide, an arm which carries an x-ray opaque targeting pin mounted within a relatively larger x-ray transparent disc. The targeting pins are then used to precisely align the drill guides with the nail screw holes. The drill guides then facilitate drilling holes through the bone in precise coaxial alignment with the nail screw holes. Last, locking screws are extended through the nail and screwed into the bone by the use of the drilled screw holes.

14 Claims, 3 Drawing Sheets

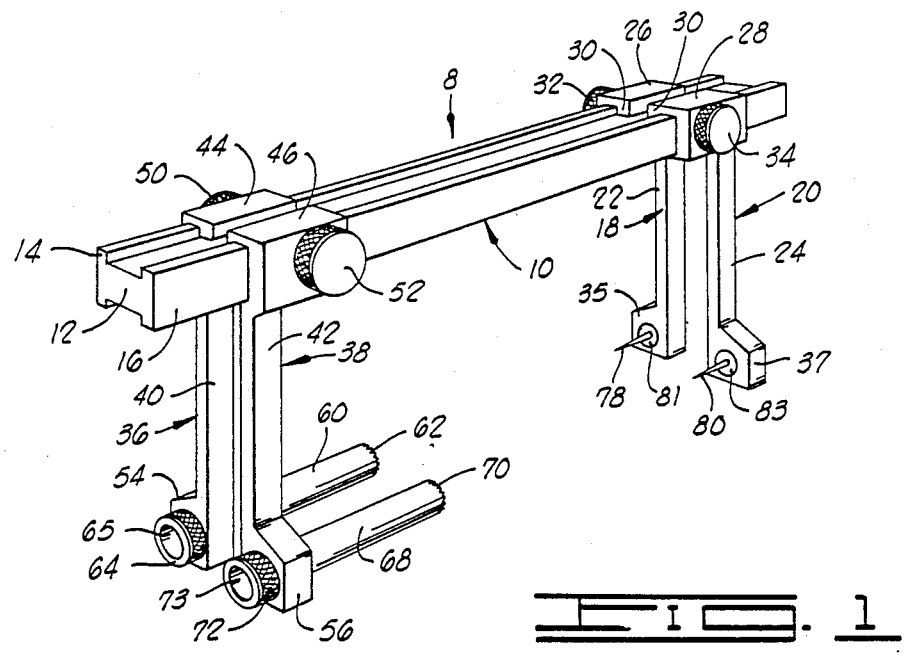
FIG. 1
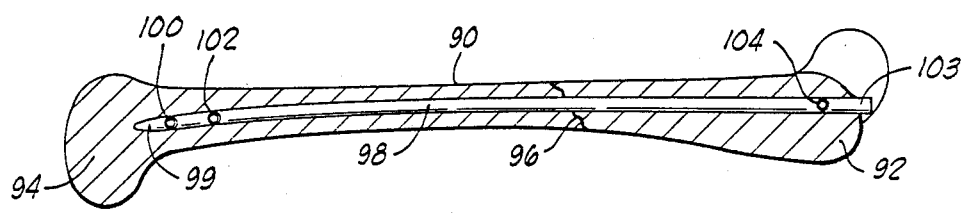
FIG. 2
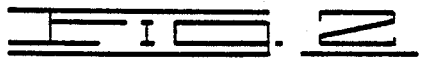
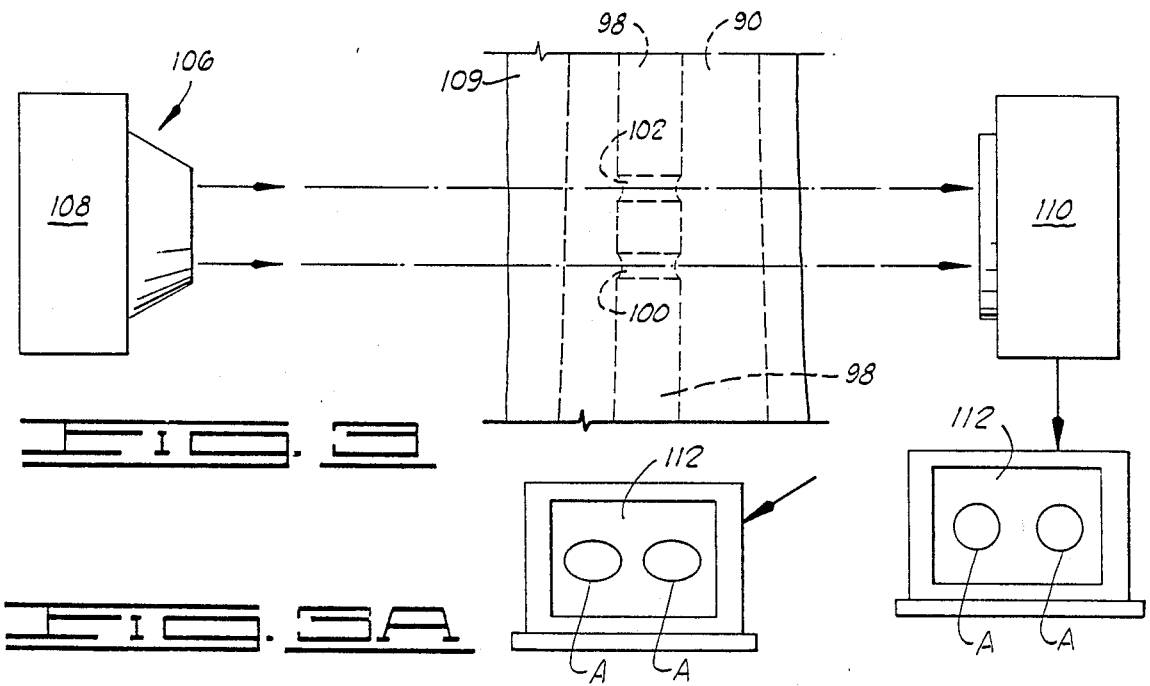
FIG. 3
FIG. 3A

APPARATUS AND PROCEDURE FOR BLIND ALIGNMENT OF FASTENERS EXTENDED THROUGH TRANSVERSE HOLES IN AN ORTHOPEDIC LOCKING NAIL

BACKGROUND OF THE INVENTION

1. Field of the Invention

This invention relates to orthopedic prostheses used to align, to draw together and to generally set long bones of the body which have been fractured, and more particularly, to a device used to assure that screws can be extended through fractured long bones of the body at a location such that the axes of the screws and the holes in the bone through which they are inserted line up precisely with the axes of screw-receiving holes formed through the distal end of an orthopedic fastening nail employed in an intramedullary position within the fractured bone of the patient.

2. Brief Description of the Prior Art

In orthopedic surgery, a technique utilized in the setting of fractured long bones of the body has entailed placing in the medulla of the fractured bone, an elongated hollow stainless steel shaft, often termed a "nail", which extends coaxially within the bone, and provides rigidity and alignment to the fractured bone. The nail is characteristically provided with transverse apertures at its opposite ends through which fastening devices, such as screws, may be passed and extended into the bone on opposite sides of the nail. The nail is thus anchored against shifting or movement relative to the bone. Since the nail is, at the time of screw implacement, located within the medulla of the bone, and the bone within the flesh of the limb that is involved, it is not possible to visually discern the location of the screw holes through the nail. It is therefore very difficult to achieve the required precision of alignment to be assured that the screws will enter the screw holes in the nail, and pass clearly therethrough on the first attempt at alignment.

For various reasons, it is much easier to successfully achieve the extension of the screw through the hole provided in the proximal end of the nail, than it is to properly align and successfully extend the screws through the pair of spaced screw holes formed transversely through the distal end of the nail. For the purpose of achieving such placement of the distal screws, various instruments have been devised and various procedures proposed. The more recent of these have involved, in general, the use of some type of drill jig which is employed in conjunction with an x-ray device to permit x-ray aligned or located drill hole paths to be accurately formed so that the screw holes provided through the bone on opposite sides of the nail are hopefully precisely aligned with the screw holes through the nail, and the screws may then be properly emplaced quickly and with no difficulty.

A recent device and technique utilized for installing an implanted orthopedic prosthesis in the form of an elongated nail or rod placed in the medulla of a fractured bone is disclosed in Taylor et al U.S. Pat. No. 4,667,664. The function of the device disclosed in this patent is to locate the blind screw holes formed in the distal end of the nail, so that the screws can be quickly and accurately extended through the screw holes and used to interlock the prosthesis with the surrounding bone.

The device used in U.S. Pat. No. 4,667,664 includes a frame adapted to be secured to the proximal end of the intramedullary nail. A target mechanism is disposed at the opposite end of the frame from that end which is affixed to the proximal end of the nail. This target mechanism is arranged so that it can be moved in four degrees of movement, thereby facilitating precise coaxial alignment with each blind screw hole through the distal end of the nail. The described four degrees of movement are each independent of each other and are, of course, movement relative to the axis of the blind screw hole. After the target mechanism has been aligned, using conjunctively a standard x-ray device, a drill is employed to drill through the bone along the indicated screw axis, with the drill bit passing successively through the blind screw holes in the distal end of the nail and into the bone on the opposite side of the nail.

In the case of the device and technique disclosed in U.S. Pat. No. 4,667,664, several manual manipulations of the target through the various degrees of freedom of movement are required prior to the time that proper alignment is achieved, and the x-ray device must either be switched on and off a number of times during this manipulation, or allowed to remain on with consequent exposure of the physician or technician to x-rays during such alignment and adjustment manipulations. It is also, of course, necessary to have adequate room or space to enable the relatively lengthy device to be attached to the proximal end of the nail and extended along the limb to the location where the distal end of the nail is approximately located.

Olerud et al U.S. Pat. No. 4,625,718 discloses an apparatus useful for forming transverse bores through a fractured bone in registry with the transverse screw holes of an orthopedic locking nail. The apparatus includes an elongated holder to accommodate an aiming member which is adapted to be brought into the beam path of an x-ray apparatus by manual manipulation of the elongated holder. A reception head is adapted to receive a drill rotatably supported in the holder. A power drive device is supported by the holder for rotatably driving the reception head, and the drill supported therein. The reception head is made of a material transparent to x-ray radiation so that proper alignment of the drill is thought to occur when the drill, as represented by a dark central bulls-eye spot, is shown by the x-ray monitor to be centered in the circular image of the reception head material transparent to x-ray radiation. The portrayal of this configuration on the monitor also requires that the drill and the reception head be coaxially aligned with the screw holes through the locking nail.

In this device, hand grips are provided to facilitate the hand manipulation of the elongated holder at a time when the beam of x-rays is projected onto the reception head, and the drill bit located toward the center of the elongated holder. There is thus exposure of the physician or his assistant to x-rays at this time. Moreover, the hand-held jig is difficult to hold steady so as to be assured that the drill is proceeding evenly and directly along a line which is coaxial with the axis of one of the screw holes formed through the orthopedic locking nail.

Cho U.S. Pat. No. 4,257,411 discloses a drill guide used for drilling a tunnel or hole through a portion of the femur in a precise manner, so that the drill exit is precisely controlled, and the drill tip is located in a very critical position for the purpose of reconstructing the interior cruciate ligament of the knee. The surgical tool drill guide disclosed in this patent is characterized in having first and second upright rods carrying tubular first and second drill sheaths on their respective distal ends in relation to a transverse mounting means on which the uprights are mounted by the use of sliding heads carried at their proximal ends. This type of jig or drill guide tool permits the first and second drill sheaths to be brought up tightly against opposite surfaces of the femur so as to provide a continuing and exact axial alignment for the drilling of the bony tunnel. The way in which the upright members which carry the drill sheaths are movably adjustable has some similarity to the present invention, as do the tubular drill guides carried at the ends of these parallel upright members.

In U.S. Pat. No. 4,541,424 to Grosse et al, there is disclosed a distal aiming device which undertakes to aim drills in a direction which is coaxially aligned with a pair of screw holes in an orthopedic locking nail. The aiming device has a portion which is detachably secured to the proximal end of the locking nail. An elongated rod or bar carries a drill or pin aiming head at one end opposite the end of the nail which has a pair of screw holes extending transversely therethrough. The aiming head is capable of being moved in a direction parallel to the axis of the orthopedic locking nail. Two adjusting pins can be extended through the aiming head in a direction normal to the axis of the locking nail, and it is possible with the aid of the aiming device to perform a pre-adjustment of the aiming head relative to the locking nail. The adjusting pins are adapted, by movement of the aiming head, to be coaxially aligned with the center axes of the two transverse bores or screw holes formed through the locking nail. All of this measurement and alignment in relation to the transverse screw holes through the locking nail is accomplished before the locking nail is driven into place in the medulla of the bone. As previously stated, the device for aligning the pins is then secured to the proximal end of the nail, and it is assumed that the axes of the bores of the aiming head through which the alignment pins first extended will still coincide with the axes of the transverse screw holes through the locking nail. A requirement for such alignment remaining true, however, is that the locking nail has not been bent or deformed during implantation. This is checked by means of an x-ray apparatus which reveals if no circular opening is depicted on the monitor of the x-ray apparatus. A readjustment of the aiming head is then necessary and is performed by repeating all of the steps, including extraction of the nail from its position within the bone. Once the proper alignment is achieved in the manner described, the hole can be drilled through the bone to enable screwing in of transverse screws through the bone and through the transverse screw holes or openings in the locking nails.

Bosacco U.S. Pat. No. 3,670,724 discloses a hip replacement prosthesis which comprises an artificial ball mounted on, or integral with, an intermediate portion which abuts the end of the bone in question. A shank or stem having a plurality of screw holes is attached to the intermediate portion and is intended for intramedullary insertion. The intermediate portion has at least one locating hole and the stem has a plurality of axially spaced holes formed therealong. Although the stem is inserted into the medulla, and its holes are therefore obscured from view, the locating holes in the intermediate portion remain exposed. Therefore, a rectangular post can be fitted into the locating holes and used to properly position a template which is attached to the post, and which carries a plurality of screw holes. These screw holes are spaced and positioned so that when they are in place, and the template is attached to the post, the screw holes in the template are congruent with, or in registry with, the holes in the stem. This then facilitates the extension of holes by drilling transversely through the template, and through the near bone cortex, through the stem holes, and finally, into the far cortex portion of the bone. After such drilling by the use of the template, the template is removed and screws are then emplaced through the aligned holes in the bone and in the stem.

This system, as described in U.S. Pat. No. 3,670,724, again depends for accuracy upon the end of the stem, where the post is located and to which the template is attached, remaining in a precisely fixed spatial relationship to the distal end of the elongated stem. This precision, of course, is decreased by any warping or distortion in either the template or the stem.

In U.S. Pat. No. 3,782,373 to Smythe, a drill jig used in conjunction with a femoral prosthesis is disclosed. The drill jig includes a blade or insert which is shaped like the shank portion of the femoral prosthesis which is to be used, and is initially fitted into, and seated in, the femur medulla in substantially the same manner as the prosthesis will be seated in the femur. The insert or blade of the jig contains one or more guide bores for a work tool which form one or more holes in the femoral bone for the purpose of accommodating the screws subsequently screwed through the bone and through aligned holes in the shank of the actual femoral prosthesis after it is fitted in place. Thus, in this case, the holes are initially drilled through the bone and the femoral prosthesis device is then inserted into the bone until the preformed holes therethrough are brought into alignment with the holes previously drilled through the bone.

Another jig used for a femoral prosthesis device used in performing hip prosthesis surgery is disclosed in Deyerle U.S. Pat. No. 3,814,089. The jig disclosed in this patent is a generally U-shaped member which carries a short leg which can be screwed or fastened to the upper end of a hip or femoral prosthesis after it has been placed in position. The femoral prosthesis carries a plurality of axially spaced holes in the blade or shank part of the prosthesis driven into the femur. The dimensions of the jig are such that once it is bolted to the top of the prosthesis, the second and relatively long leg of the jig, which will extend down outside the leg of the patient, will have a plurality of axially spaced holes therein precisely aligned with those holes carried in the blade part of the femoral prosthesis already in place. It is therefore possible to use the holes through the jig to guide the drill in drilling through the bone in alignment with the axes of the several holes formed in the prosthesis. Since the jig structure is releasably assembled to the head or the top of the prosthesis, it can be quickly removed after the holes have been drilled, and the pins placed in position.

This type of jig can be considered fairly reliable because of the relatively short distance from the point that it attaches to the femoral prosthesis to the location of the holes in both the prosthesis and the long leg of the jig. This allows little opportunity for misalignment.

U.S. Pat. No. 4,570,624 to Wu discloses a universal guide device for inserting parallel pins, which device includes an elongated bar having a plurality of blocks slidable along the bar, and adapted to be adjustably locked in position on the bar. A transverse opening is formed through each of these blocks so that the openings through the blocks are parallel to each other. A removable sleeve is provided, and has a complementary external configuration corresponding to the internal configuration in the opening or bore through each block. Each of these sleeves has a serrated end face for engagement with the bone for holding the sleeve in position at a time when a drill stem is extended through the opening for drilling a hole for the purpose of inserting a surgical pin in the hole formed by the drill. The sleeving may be changed out according to the diameter of the drill bit to be used.

In Ulrich U.S. Pat. No. 4,292,964, a method and apparatus for pinning a fractured pelvis is disclosed. The apparatus is a jig or guiding apparatus which includes an elongated member provided with a pair of longitudinally spaced, transversely projecting arms slidable along the elongated member. These arms have outer ends which are provided with coaxially aligned cannulas having points directed at each other and separated by a space. The fractured bone is positioned in the space between the cannulas with the points engaging the fractured bone. Holes are formed in the bone surface by drilling through the cannulas.

Next a relatively small guide rod is inserted axially through the cannulas and through the fractured bone which is engaged between the cannulas. The guide apparatus is then disengaged from the bone, but the small diameter guide rod is left in place in the bone, and a tubular drill bit is fitted over one end of the guide rod and a bore is drilled through the bone along the guide rod while the bit is guided through the bone along this rod. The guide rod is then withdrawn from the bit which itself is left in the bore through the fractured bone. Finally, the bit is pushed axially out of the bore that it has formed, and is replaced by a bone pin whose ends are axially oppositely braced against the opposite ends of the fractured bone. This patent, while interesting for the drilling and pinning technique disclosed, is not concerned with alignment of drill holes with blind screw holes formed in the end of an orthopedic nail which is obscured from view until the time that the screws are actually extended through the screw holes therein.

BRIEF DESCRIPTION OF THE PRESENT INVENTION

The present invention provides a surgical technique or procedure and an adjunct apparatus or device by means of which surgical pins or screws can be implanted at a precise and critical location in the body for the purpose of locking an orthopedic nail in a position to strengthen or reinforce or limit movement of a fractured bone.

Broadly described, the apparatus or device used in the invention may be termed a jig in that it is set in a precise reference or indexing position, and is used to facilitate forming holes through the skin and bone of the body at a location precisely coaxially aligned with locking screw holes in the distal end of an intramedullary orthopedic nail. The jig is used in conjunction with a source of x-rays, such as a fluoroscope.

Initially, a fluoroscope is used to identify points on the skin of a patient which are located on lines projected directed through screw holes in the distal end of an orthopedic nail located in the fractured bone of the patient. These points are memorialized by marking their locations on opposite sides of the fractured limb with visible indicia. Incisions are then made from the marks so located on one side of the limb inwardly to the bone. The jig, having a pair of tubular drill guides, is then set in position against the bone by extending the tubular drill guides through the incisions. The jig is clamped on opposite sides of the leg so that the pair of spaced, parallel tubular drill guides which it carries are approximately coaxially aligned with the screw holes through the orthopedic nail. The fluoroscopic device is next again used to beam x-rays at the jig device and the leg so that the x-rays pass through the bores in the tubular drill guides and through the screw holes formed in the orthopedic nail. If an image produced on a display device or monitor indicates that the x-ray-transparent hollow interiors of the tubular drill guides precisely aligned with the axes of the screw holes in the nail, drilling can then proceed and the screws set in position.

In a unique aspect of the present invention, small, visible marks are made on the skin of the patient after the first sighting in with the fluoroscope through the tubular drill guides, and these marks are then used to achieve an initial clamped setting of the tubular drill guides against the side of the bone. This position is then checked again with the fluoroscope to assure that there is precise coaxial alignment of the drill guide sleeves with the screw holes through the orthopedic nail.

An important object of the invention is to permit screw holes to be drilled through the distal end of a fractured long bone of the body, such as the tibia or femur, at a location that such screws extended through the drilled holes will also pass easily and precisely through aligned holes in the end of an orthopedic nail used at that location.

A further object of the invention is to allow an orthopedic surgeon to precisely align drill holes with holes through an orthopedic nail with minimum exposure to x-ray emanations used intermittently in the procedure.

Additional objects and advantages of the present invention will become apparant when the following detailed description of a preferred embodiment of the invention is read in conjunction with the accompanying drawings which illustrate such embodiment.

GENERAL DESCRIPTION OF THE DRAWINGS

FIG. 1 is a perspective view of the jig used for sighting in, aligning and guiding drills used for drilling holes through the flesh and bone of a fractured limb in alignment with screw holes provided in an orthopedic nail disposed in an intramedullary position within a fractured bone.

FIG. 2 is a longitudinal sectional view through a long bone of the body which has been fractured, and which has had an orthopedic nail emplaced in the medulla thereof.

FIG. 3 is a plan view illustrating, partially schematically and partially in elevation, a technique utilizing a fluoroscopic device for aligning a beam of x-rays with the axes of a pair of screw holes having parallel axes, and formed through the distal end portion of an orthopedic nail. The nail is shown in dashed lines as it is implanted in a fractured bone, also shown in dashed lines, and the limb which is fractured is shown in full lines.

FIG. 3A depicts the appearance of an x-ray generated image on a fluoroscopic readout or monitor at a time when the fluoroscope-generated x-rays are not being transmitted along lines which are coincident with the axes of the screw holes through the orthopedic nail; that is the fluoroscopic device is not properly aligned with the screw hole axes.

Figure 4:
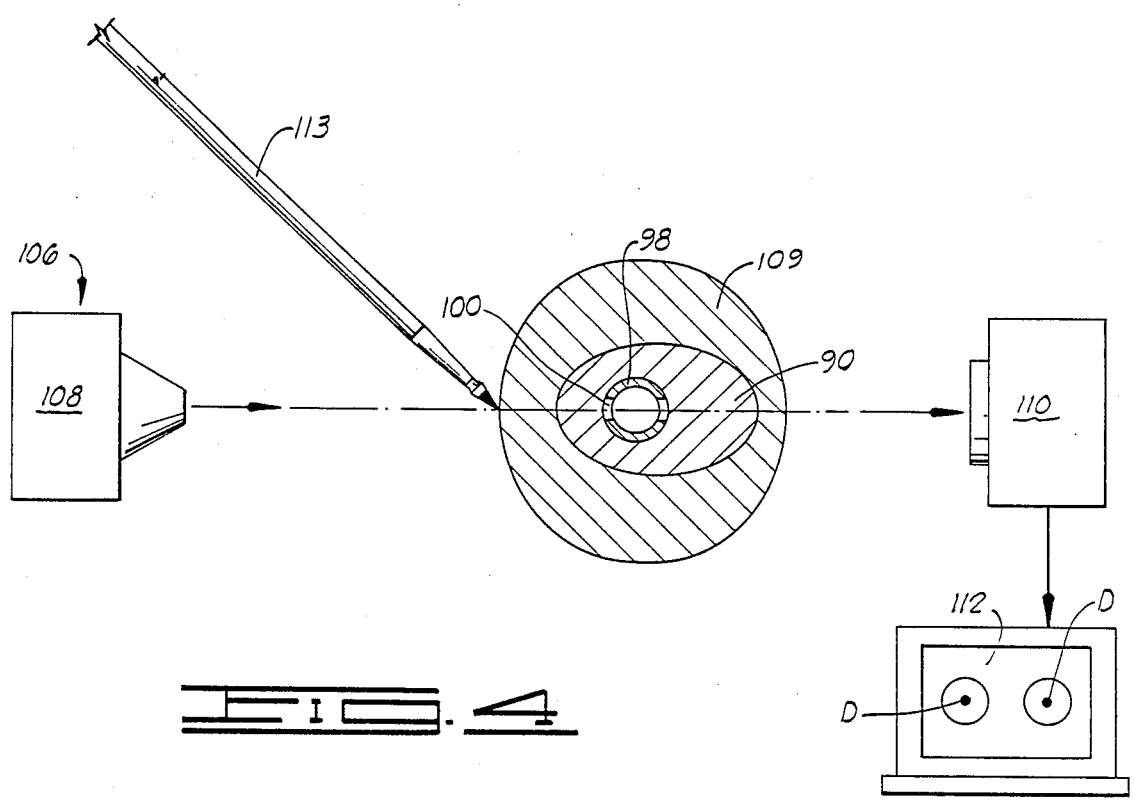

FIG. 4 is a side elevation view illustrating the position of the fluoroscope relative to the fractured bone, orthopedic nail and limb in which the fractured bone is located as such is shown in plan view in FIG. 3, but illustrating in FIG. 4, a second step of the process of the invention in which the fractured limb is marked at the point where the x-rays are transmitted into the limb, and emerge from the limb at a time when the x-rays from the fluoroscope are properly colinearly aligned with the axes of the screw holes through the orthopedic nail.

Figure 5:
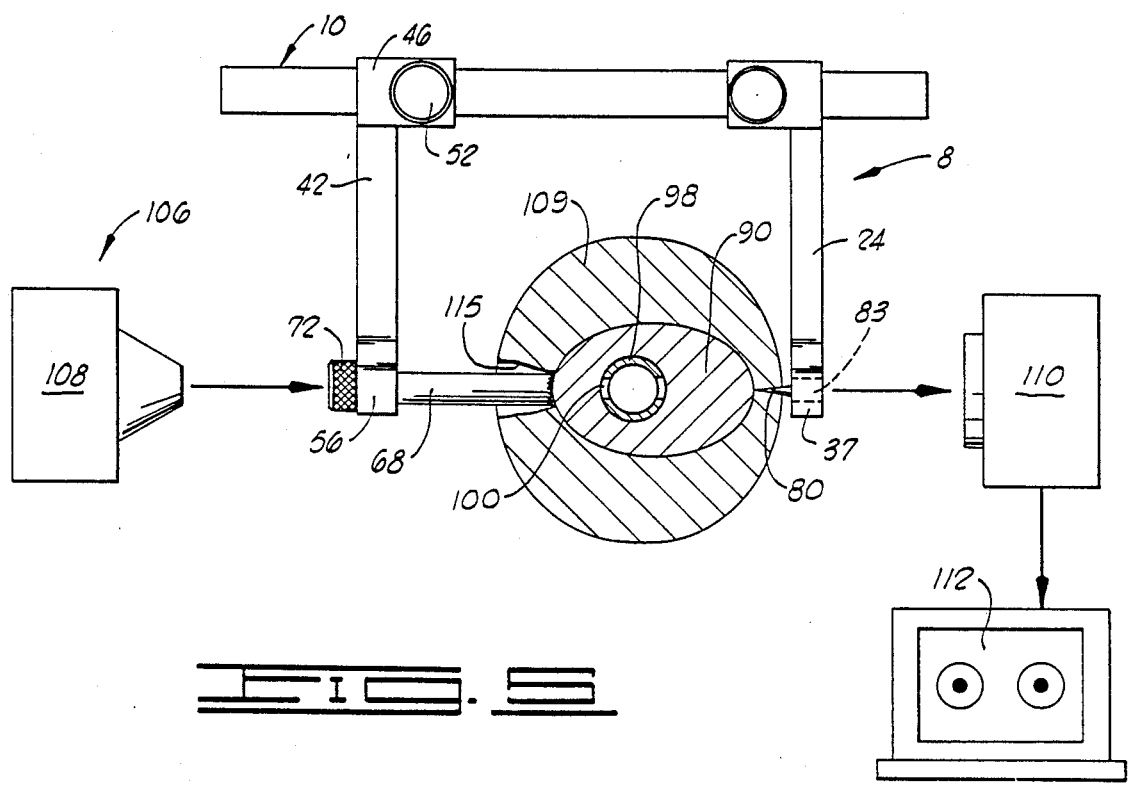

FIG. 5 shows the status of the fluoroscopic device and the screw aligning jig of the invention at a later stage in the process of the invention, at which later stage the screw guiding sleeves of the jig have been set against the bone at a location aligned with the screw holes through the nail.

Figure 6:
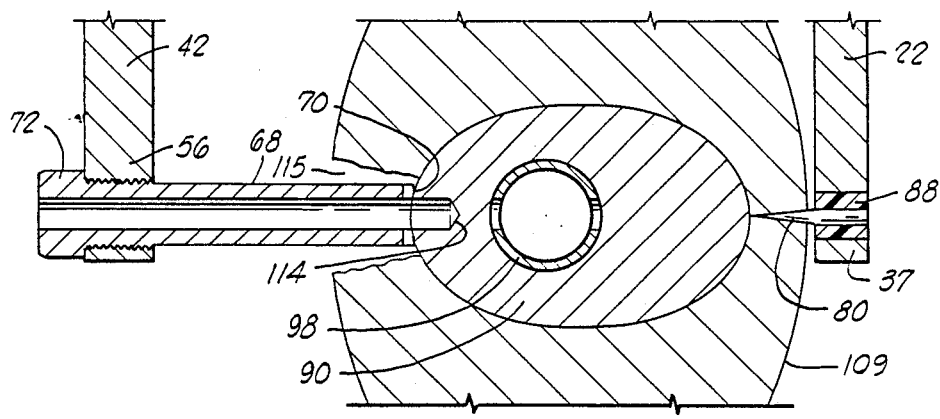

FIG. 6 is a sectional view shows the screw-aligning jig of the invention at an intermediate stage during the process of the invention, at which stage the jig is set on opposite sides of the fractured bone, and with certain elements of the jig in alignment with the fastener holes through the elongated nail, and preparatory to commencing to drill through the bone in order to place the holes for the fasteners through the bone in alignment with the fastener holes in the orthopedic nail.

Figure 7:
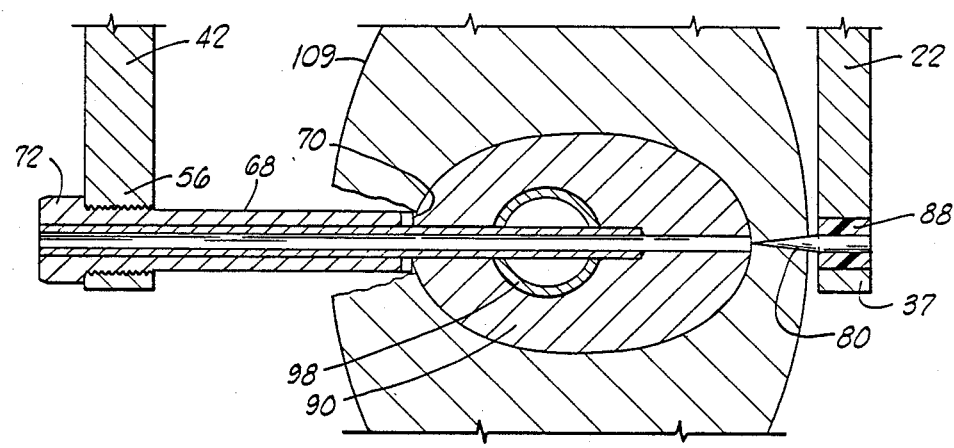

FIG. 7 is a view similar to FIG. 6, but illustrating the status of the jig and the fractured bones after a drill guide has been inserted in an initial hole drilled in the bone, and then a second hole has been drilled in the bone in order to accommodate a fastener to be extended through the bone and through one of the fastener holes formed in the orthopedic nail.

Figure 8:
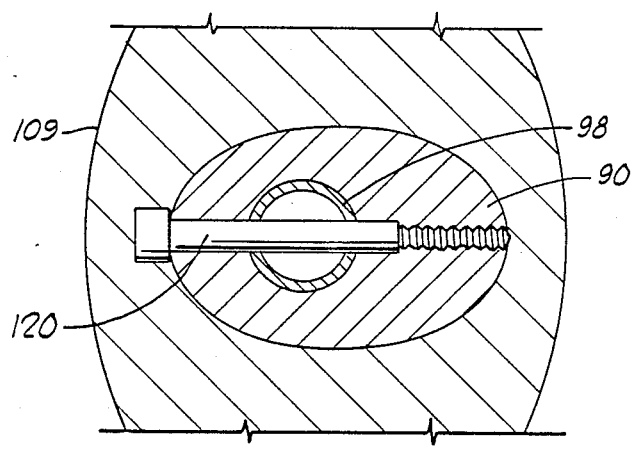

FIG. 8 is a sectional view of the limb which contains the fractured bone, the orthopedic nail and the fastening screws which are extended through the orthopedic nail holes and aligned holes in the bone to lock the orthopedic nail in position.

DETAILED DESCRIPTION OF A PREFERRED EMBODIMENT OF THE INVENTION

FIG. 1 is a perspective view of a jig 8 used in carrying out the method of the invention. The jig 8 is employed for sighting in, aligning and guiding drills used for drilling holes through the flesh and bone of a fractured limb in precise alignment with screw holes provided in an orthopedic nail disposed in an intramedullary position within the fractured bone. The jig 8 is also subsequently used for initially guiding the screws as they are emplaced through the bone and through the screw holes in the orthopedic nail.

The jig 8 used for the purposes described includes an elongated channel element 10 which has a central web portion 12 bounded by a pair of opposed tracking flanges 14 and 16 located at opposite sides of the web portion 10 and imparting an I-beam configuration to the channel element.

There are then mounted on the channel element 10 in sliding engagement with the tracking flanges 14 and 16, two pairs of indexing standards. Thus, near one end of the channel element 10 a pair of indexing standards 18 and 20 are located. Each standard includes an indexing leg 22 or 24, and each includes a C-shaped sliding indexing head. These indexing heads are denominated by reference numerals 26 and 28. Each indexing head 26 and 28 includes a flange 30 which slidably engages one of the respective flanges 14 and 16. Each flange 30 cooperates with a lower flange (not visible) of the same indexing head in engaging one of the respective flanges 14 or 16 so that the indexing heads cannot wobble, cant or skew as they slide along flanges 14 and 16. A pair of set screws 32 and 34 extend through the sides of the respective indexing heads 26 and 28 and can be tightened by turning the knurled knobs thereof so as to precisely set the indexing heads 26 and 28 the indexing standards 18 and 20 of which they are a part at a selected location along the channel 10. At its lower end, the indexing leg 22 carries a pin-carrying foot portion 35. Similarly, a pin-carrying foot portion 37 is carried on the lower end of the leg 24.

Near the opposite end of the elongated channel element 10, the second pair of indexing standards 36 and 38 are disposed and slidably engage the channel element. The indexing standards 36 and 38 are slidable independently of each other, and each includes an elongated leg; the indexing standard 36 carries leg 40 and the indexing standard 38 carries leg 42. The parallel legs 40 and 42 of the respective standards 36 and 38 are formed integrally with indexing heads 44 and 46 at their upper ends. Each indexing head 44 and 46 is substantially C-shaped in configuration so that it can closely engage the respective tracking flange 14 or 16. This prevents wobbling or canting of the respective indexing head on its respective flange as it is slid along the flange of the elongated channel element 10. When the legs 40 and 42 have been brought to a selected location in a manner and for a reason hereinafter described, the indexing standards 36 and 38 are then fixed in position by setting a pair of set screws 50 and 52 having knurled finger tabs.

At the lower end of the leg 40 of the indexing standard 36, the leg is joined to a tube-receiving foot portion 54 which has an internally threaded bore or passageway therethrough (not visible), with the axis of this bore or passageway extending parallel to the axis of the elongated channel element 10. This threaded bore functions to receive an elongated tubular drill guide 60. The tubular drill guide 60 is cylindrical in configuration and terminates at one end in a serrated end face 62. At its other end, the tubular drill guide 60 has a knurled finger knob 64 which facilitates rapid threading of the tubular drill guide 60 into the internally threaded bore through the foot portion 54. It will be noted that the finger knob 64 has a centrally disposed aperture 65 therethrough which is axially aligned with the axis through the tubular guide 60.

The indexing standard 38 also has a tube-receiving foot portion 56 located at the lower end of the indexing leg 42. This foot portion carries an internally threaded aperture or bore which threadedly receives the externally threaded peripheral surface of an elongated tubular drill guide 68. The drill guide 68 extends parallel to the drill guide 60, and carries a serrated end face 70. At its opposite end, the drill guide 68 carries a knurled finger knob 72 which can be used to manipulate the tubular drill guide 68, and the knurled finger knob is provided with a central bore or opening 73 therethrough which is aligned with the axis of the cylindrical tubular drill guide.

As the indexing heads 46 and 48 are slidably moved along the elongated channel element 10, they can be moved independently of each other, and they carry with them their respective indexing legs 40 and 42 and indexing foot portions 54 and 56, all forming parts of the respective indexing standard 36 or 38. Such movement also causes concurrent movement of one or both of the parallel tubular drill guides 60 and 68, and the movement of these two elements is always parallel with respect to the axis of the elongated channel element 10.

A pair of elongated sharply pointed pins 78 and 80 are disposed in precise linear alignment with the axes of the tubular drill guides 60 and 68. The pins 78 and 80 are mounted in the respective foot portions 35 and 37 which are formed on the lower ends of the respective indexing legs 24 and 22 of the respective indexing standards 18 and 20.

The method of mounting the pins 78 and 80 in the foot portions 35 and 37 is important to carrying out the method of the present invention. Thus, each pin 78 and 80, although itself x-ray opaque, is mounted securely and fixedly in the center of a small disc or cylinder of x-ray transparent synthetic resin material 81 or 83. This arrangement results in a visually contrasting pattern on an x-ray display panel, which contrasting pattern resembles a bulls-eye target, with the material in the disc or cylinder which is x-ray transparent causing the outer portion of the target to be relatively lighter, and the pins 78 and 80 causing the development of the bulls-eye central dot. This explanation will be more thoroughly understood from the ensuing description when reference is made to FIGS. 3, 3a and 4 of the drawings.

In FIG. 2 of the drawings, one of the long bones 90 of the body, such as the femur or tibia, is illustrated in cross-section and the orthopedic nail of the invention is shown disposed in an intramedullary position within the bone. The bone 90 terminates in a proximal end 92 and a distal end 94. The bone 90 displays a fracture at 96. An elongated hollow orthopedic nail or shaft 98 is driven into the medulla of the bone so that the distal end 99 of the nail 98 is near the distal end of the bone. The distal end of the nail carries a pair of screw apertures 100 and 102, and the proximal end 103 carries a screw aperture 104.

The problem which is addressed by the present invention is that of enabling the orthopedic surgeon to accurately drill a pair of screw holes through the bone 90 at precisely the correct location. These drilled screw holes extend transversely to the axis of the bone, and to the axis of the orthopedic nail 98, and they must be in the precise position which is required to align them coaxially with the screw holes 100 and 102 in the nail. This will then allow screws to be extended through the screw holes in the nail and into the bone on opposite sides thereof as a result of the accurate formation, by drilling, of the screw holes into the bone. Once the orthopedic nail 98 is placed in its intramedullary position within the bone 90, the surgeon cannot visually observe the nail at its distal end, and he therefore cannot visually determine the location of the screw holes 100 and 102.

In order to permit the surgeon to precisely locate the lines along which he should drill to establish screw holes through the bone 90 in alignment with screw holes 100 and 102 through the orthopedic nail 98, the initial step entails the use of x-ray emanations developed by a fluoroscope assembly illustrated in FIG. 3 by reference numeral 106. The fluoroscope assembly 106 has a head 108 constituting a source of x-rays which can be directed relatively precisely toward a specific target.

The fluoroscope assembly 106 also has a receiving module 110 which functions to receive or respond to x-rays transmitted from the head 108 and to develop appropriate signals indicative of the structures or elements "seen" by the x-rays in transient from the head to the receiver. In other words, the signal developed by the receiver will be correlated to those structures or elements interposed in the path of the x-rays which are transparent to the x-rays, and also elements or objects which are opaque to the x-rays. Such opaque materials then give a contrasting image at a readout display 112 or monitor of the fluoroscope assembly 106 so that the physician can determine by visual examination of the readout display panel what is being interposed in the path of the x-rays from the fluoroscope, and the spatial and alignment relationships of the several elements which are disposed in such path.

In carrying out the first step of the method of the invention, the fluoroscope assembly 106 is placed so that the head 108 is on one side of the fractured limb 109 in approximate alignment with the location within the limb where the screw apertures or holes 100 and 102 are formed through the orthopedic nail 98. The leg 109 is, of course, immobilized at this time and is retained in a fixed position. The receiving module 110 is located on the opposite side of the limb in a position to intercept x-rays which impinge upon the receiving module after passing through the limb and the distal end of the fractured bone. These x-rays also are intercepted in part by the orthopedic nail 98 and some of them are obstructed by the x-ray opaque portion of the nail, and others are able to pass without obstruction through the x-ray-transparent screw holes 100 and 102.

The fluoroscope assembly 106 is used in this first step of the invention to align the head 108 so that it directs the x-ray beam precisely along lines of propagation which are coincident with the axes of the screw holes 100 and 102 through the orthopedic nail. Any skewing or angling of the direction of propagation of the x-rays can be discerned by reference to the image portrayed on the readout device or monitor 112. At a time when the x-rays are passing directly through the screw holes 100 and 102 along lines which are in colinear alignment with the axes of these screw holes, perfectly round images will be displayed on the monitor 112 and such are shown at A in FIG. 3.

If the head 108 is angled slightly with respect to the axes of the holes 100 and 102, so that the x-ray beam is not precisely aligned with the axes of these screw holes, then the appearance of the screw hole images A on the monitor 112 will be an elliptical or oval shape, as shown in FIG. 3A, rather than the perfectly circular shape in correspondence to the precise circular cross-sectional configuration of the screw holes 100 and 102. Slight adjustments are made in the positioning of the fluoroscopic head 108 until such time as the image portrayed on the monitor 112 indicates that the x-rays are being transmitted along lines which are in precise alignment with the axes through the round cross-sectioned screw holes 100 and 102.

After this alignment has been achieved, the physician then takes an elongated scribing device which carries a marking implement at one end (such as crayon or ink dispensing head), and which also has a shaft of sufficient length to allow the hand of the physician to be out of the field of the x-rays and thus not exposed to the x-ray emanations. Such a marking device 113 is schematically illustrated in FIG. 4 of the drawings. Using such a device, the physician then marks a point on the skin of the patient where, according to the fluoroscope assembly monitor 112, such point is disposed immediately in the center of the circle which is representative of one of the screw holes. The marking procedure is then repeated for the second of these circles so that a second mark is made on the skin of the patient in a way such as to form a bulls-eye in the second circle representing the circular cross-section through the second of the screw holes. The person using the marking device 113 is aided in making these markings by the fact that the point will be somewhat opaque to the x-rays, and thus can be guided into the center of the imaged circular area which represents an x-ray transparent zone equivalent to the open cross-sectional area of each screw hole. The appearances of the images which appear upon the monitor 112 following such marking is shown in FIG. 4 where the black dots, D, in the centers of the bulls-eyes represent the marks which have been made on the skin of the limb 109.

This marking procedure is then repeated by making two marks on the opposite side of the limb 109 containing the fractured bone. These marks are also disposed in the lines of the x-ray beam through the screw holes 100 and 102, as evidenced by the fact that these markings, too, are guided into and centered within the two circular areas corresponding to the x-ray transparent cross-sectional area of the two screw holes.

After the markings or indicia have been placed on the skin, using the described technique in which the x-rays from the fluoroscope assembly are used for precise mark alignment, the fluoroscopic head 108 is locked in position, as are the other components of the fluoroscope, so that the x-rays will again be transmitted along lines which are in precise alignment with the axes of the screw holes 100 and 102 in the nail 98 at a time when the fluoroscope assembly is re-energized later in the process of the invention.

After the marks have been made on the flesh of the patient in the manner described, incisions are made where such marks have been made on the skin. The described incisions are made through the flesh of the limb to the bone 90, thereby permitting the tubular drill guides 60 and 68 to be extended through the incisions until the serrated end portions of these tubular drill guides contact the surface of the bone. This relationship is shown in FIG. 5 where an incision 115 has been made in the flesh adjacent the bone 90 to allow the tubular drill guide 68 to be extended through the incision and into contact with the bone surface.

The tubular drill guides 60 and 68 are, of course, moved through their respective incisions by sliding the indexing heads 44 and 46 thereof along the elongated channel element 10 until such contact with the bone occurs. The set screws 50 and 52 are then tightened to fix the location of the indexing standards 36 and 38. At this time, the elongated pins 78 and 80 may be impaled in the flesh to any desired depth, so long as they function to fix the location of the opposite side of the jig, and particularly the pins, at the same location where marks have previously been made on the skin when the pins were in proper alignment with the screw holes 100 and 102 through the nail 98, as indicated by the fluoroscope monitor.

After the tubular drill guides 60 and 68 and the pins 78 and 80 have been positioned as illustrated in FIG. 5, the fluoroscope assembly 106 is then again brought into position to propagate x-rays along parallel lines colinear with the axes of the tubular drill guides 60 and 68, the axes of the aligned screw holes 100 and 102, and containing points represented by the points of pins 78 and 80. As previously described, when the alignment is correct and the axes of the tubular drill guides 60 and 68 are coaxially aligned with the axes of the screw holes 100 and 102, circular bulls-eye images of the type shown in FIG. 5 are developed on the display monitor 112. Thus, the perfectly concentrically disposed bulls-eyes within the surrounding larger circles of contrasting lesser darkness are indicative of proper alignment of the tubular drill guides 60 and 68 with the screw holes 100 and 102 through the orthopedic nail.

In the next step performed by the orthopedic surgeon, a drill bit is extended through each of the drill guides 60 and 68, and the cortex or hardened outer portion of the bone 90 is penetrated in each case by the drill bit to the location shown in FIG. 6, and there denominated by reference numeral 114. At this location, the cortex has been substantially entirely penetrated by the drill, and the relatively soft, spongy bone material, or cancellous, is exposed at the end of the drilled hole.

In the next step of the procedure, the physician inserts a cylindrical sleeve 116 within each of the tubular drill guides 60 and 68 so as to form a smaller diameter elongated tubular guide structure. The sleeved drill guides then function to guide a relatively smaller diameter drill bit used to form the remainder of the screw hole. The relatively smaller diameter drill bit passes easily through the spongy cancellous of the bone, and as a result of the previous sighting in, and alignment of, the tubular drill guides with the axis of the screw holes 100 and 102, the small drill bit will pass through the screw hole to the opposite side of the nail. There the bit will pass easily through the spongy part of the bone until reaching the denser bone in the cortex part of the bone. Drilling will then be continued and the relatively small diameter bore formed by the small diameter bit will be projected to the opposite side of the bone where the point of the small drill will emerge from the bone 90. The fact that the drill has traversed the bone can, of course, be discerned from the feel of the drill during the drilling.

The small drill is then retracted and removed from the tubular drill guide 60, and later from the drill guide 68 after the second hole has been drilled. A linear gauge element can then be inserted through each bore hole which has been formed by the relatively large diameter drill and the projected small counter-bore formed by the smaller diameter drill bit until the gauge reaches the opposite side of the fractured bone from the side contacted by the serrated end faces of the drill guides. The drill guides 60 and 68 and the linear gauge can then be removed from the limb by sliding the pins 78 and 80 to the right, and allowing the jig 8 to be then removed from the limb.

As a result of the known length of the tubular drill guides 60 and 68 and the known length of the linear gauge extended therethrough to the opposite side of the bone, it is possible to then calculate, with precision, the length of the orthopedic screws 120 which should be placed in position to lock the orthopedic nail in the bone, and prevent its movement and thus stabilize the bone in relation to the rigid elongated nail. The screw is easily emplaced by simply extending it through the incision and drilled holes which have been formed through the flesh and bone, respectively, in alignment with the screw holes 100 and 102 in the orthopedic nail. FIG. 8 illustrates the appearance of the screw after it has been emplaced transversely through the orthopedic nail, and transversely of the bone. It will be noted that the relatively spongy and soft cancellous portion of the bone 90 has offered insignificant resistance to extending the large diameter part of the screw beyond the terminus of that portion of the screw hole which has been drilled with the relatively large diameter drill. Thus, the large diameter portion of the screw traverses the nail by passage through the screw hole therein, but terminates short of the dense and hard cortex portion around the outer portion of the bone at the opposite side of the orthopedic nail. The latter part of the bone is traversed by the externally threaded, relatively small diameter portion of the screw.

The surgical technique and procedure which has been described can be carried out advantageously as compared to those emperical alignment procedures previously used. While there is a small amount of empericism entailed in the use of the present invention at the outset of the procedure when the physician is roughly aligning the jig 8 with the approximate location where it is estimated that the screw holes in the orthopedic nail are to be found within the bone of the patient, the technique is thereafter relatively precise and alignment is maintained at all times without significant exposure to x-ray radiation. The initial x-ray projections and the images developed on the monitor will provide a high probability of precise alignment on the first adjustment at a time when the x-ray generator has been deactivated. Certainly no more than two adjustments will be required to achieve precise alignment of the tubular drill guides with the axes of the holes through the orthopedic nail and with the pins on the opposite sides of the limb. The marking of the points on the skin as described then permit incisions to be made to accommodate the re-positioning of the drill guides immediately against the bone of the patient. Assurance is then gained that precise coaxial alignment of the axes of the tubular drill guides and the axes of the screw holes is maintained by again looking at such alignment by the use of the fluoroscope. The physician is not exposed to radiation during this check of alignment.

Any slight misalignment can be quickly corrected at a time when the fluoroscope is turned off, followed by one final recheck using the fluoroscope. Drilling then proceeds and can be quickly and easily completed without fear of any necessity to excessively traumatize the patient by drilling unnecessary and useless drill holes into the bone.

Although a preferred embodiment of the invention has been herein described in order to illustrate the manner in which the basic principles of the invention enable the objectives of the invention to be achieved, it will be understood that some changes, particularly in the apparatus and jig which has been described, can be made without departure from these basic principles. Changes and innovations of this type are therefore deemed to be circumscribed by the spirit and scope of the invention, except as the same may be necessarily limited by the appended claims or reasonable equivalents thereof.

What is claimed is:

1. A device for use in directing drill holes transversely through a fractured long bone of the body in alignment with a pair of spaced, transverse holes through an elongated orthopedic nail emplaced in the medulla of the fractured long bone comprising:
    an elongated channel element having first and second end portions;
    a first pair of indexing standards slidably secured to one end portion of said channel element for independent sliding movement in an axial direction therealong, each of said indexing standards in said first pair including:
        means for releasably locking the indexing standard at a selected fixed position along said elongated channel element;
        a foot portion spaced from said channel element;
        a leg connecting said foot portion to said channel element, and spacing said foot portion from said channel element; and
        an elongated tubular drill guide mounted on said foot portion and extending parallel to said elongated channel element, said elongated tubular drill guides of said indexing standards in said first pair extending parallel to each other;
    a second pair of indexing standards slidably secured to the second end portion of said elongated channel element for independent sliding movement in an axial direction therealong, each of said indexing standards in said second pair including:
        means for releasably locking the indexing standard of said second pair at a selected fixed position along said elongated channel element;
        a foot portion spaced from said channel element;
        a leg connecting said foot portion to said channel element;
        a pin disc of x-ray transparent material mounted in said foot portion of each one of said indexing standards in said second pair of indexing standards; and
        an elongated x-ray-opaque pin mounted in the center of said pin disc and having its longitudinal axis extending parallel to said channel element, and to said tubular drill guides on the foot portions of said first pair of indexing standards, the longitudinal axis of one of said elongated pins being aligned with the longitudinal axis of one of said tubular drill guides in a line extending parallel to a line colinear with the aligned longitudinal axis of the other of said elongated pins and the other of said tubular drill guides;
    said legs of said indexing standards having a length such that said foot portions will be spaced from said channel element by a distance sufficient to allow said channel element to bridge across a leg in which the fractured bone is located when said elongated pins touch the skin on one side of the leg in which the fractured bone is located, and said tubular drill guides touch the leg in which the fractured bone is located on the opposite side thereof from the side upon which said pins are located and touch the leg.

2. A device for use in directing drill holes transversely through a fractured long bone as defined in claim 1 wherein said means for releasably locking the indexing standard comprises a set screw extended through a portion of said indexing standard and against said elongated channel element to prevent further axial sliding movement along said channel element by said indexing standard.

3. A medical procedure for determined the location of a transverse fastener hole in an end of an orthopedic nail placed within the medulla of a fractured long bone of a limb in order to fix the location of the nail in the bone prior to drilling through the bone and positioning a fastener through the drill hole and the fastener hole in the orthopedic nail, said procedure comprising:

maintaining the limb and fractured bone in a fixed position;

projecting x-ray radiation through the limb, through the fractured bone and through the fastener hole in the nail, and onto an x-ray monitor;

adjusting the path of projection of the x-ray radiation relative to the limb, the bone and the orthopedic nail and the fastener hole through the nail so that the ray-image produced on said x-ray monitor visually indicates to an observer of the monitor that the projected X-ray radiation is traveling in lines which are in colinear alignment with the axis of the fastener hole in the nail;

securing and fixing the source of x-ray radiation so that the described travel of the x-ray radiation in colinear alignment will be automatically resumed and precisely reinstated at any time when the x-ray radiation is re-developed and against projected through the limb, through the fastener hole in the nail and onto the x-ray monitor;

placing indicia on the surface of the skin on the fractured limb at locations on opposite sides of the limb where the x-ray monitor indicates x-rays traveling in the described colinear alignment are entering and exiting the fractured limb, and accomplishing such visible indicia placement concurrently with the projection of x-ray radiation through the fractured limb, and using such radiation to effect such placement;

terminating the x-ray radiation while maintaining the secured, fixed position of the source of x-rays relative to the limb, bone, orthopedic nail and x-ray monitor;

placing a tubular drill guide and an elongated x-ray opaque pin in a jig in which both said drill guide and said elongated x-ray opaque pin are carried slidably on an elongated channel for movement in a direction parallel to the longitudinal axis of said elongated channel and toward and away from each other, said drill guide and elongated pin being spaced from the channel by legs which slidably support the guide and pin on the channel, and permit the channel to bridge across the limb containing the fractured bone when said tubular drill guide contacts the fractured bone on one side thereof and the elongated pin contacts the fractured limb on the other side thereof;

while said radiation is terminated, incising the skin of the fractured limb at the precise location of the indicia placed on the surface of the skin on the side of the limb facing the source of x-ray radiation to a depth of incision sufficient to permit said tubular drill guide to be directed axially through the incision and along a line extending between the indicia placed on the skin on opposite sides of the fractured limb until one end of the tubular drill guide touches the fractured one;

placing the jig relative to the limb so that the point of said elongated x-ray opaque pin touches the indicia on the opposite side of the limb from the side which faces the source of x-ray radiation, and said tubular drill guide is extended through said incision along its projected axis to a location where the tubular drill guide is fixed against, and in contact with, the fractured bone and in said incision with its axis colinear with a line projected through the hole in the nail and to the point of the elongated x-ray opaque pin;

projecting x-ray radiation from said source through the tubular drill guide and through the fastener hole in the orthopedic nail to indicate the state of alignment of the axes of the tubular drill guide and the fastener hole while the drill guide extends through the incision and into contact with the bone; and coaxially aligning the tubular drill guide axis and the fastener hole axis by adjusting the position of the tubular drill guide as needed to achieve such coaxial alignment and as indicated by said x-ray monitor; then after ceasing the projection of x-rays, placing a fastener through said drill guide along its axis and into the fastener hole in the orthopedic nail along said fastener hole axis.

4. A medical procedure for determining the location of a transversely extending, elongated fastener hole in the distal end of an orthopedic nail placed within the medulla of a fractured long bone of a limb in order to fix the location of the nail in the bone prior to drilling of the bone and positioning a fastener therethrough and through said fastener hole, said procedure comprising:

maintaining the limb and fractured bone in the same position through the procedure;

beaming x-ray radiation from a source of x-rays located on one side of the fractured bone-containing limb linearly and transversely through the limb, through the fractured bone and through the fastener hole in the orthopedic nail to the side of the limb which is opposite the source of the x-rays;

adjusting the position of the source of x-ray radiation relative to the limb, the bone and the nail so that an x-ray image produced on an x-ray monitor visually indicates that the projected x-ray radiation is traveling in colinear alignment with the axis of said elongated fastener hole in the nail;

placing indicia on the skin of the limb at locations on opposite sides of the limb, using said x-ray monitor in conjunction with projected x-rays from said source to indicate when said x-rays are traveling in colinear alignment between said indicia and the axis of the elongated fastener hole in the nail as the x-rays enter, pass through and exit from the fractured limb;

positioning adjacent the limb an x-ray opaque pin having a diametric size less than the size of the diameter of the nail fastener hole so that said pin is aligned with said indicia marked on the limb on opposite sides of the limb, with said pin contacting the indicia which has been marked on the limb opposite the source of said x-ray radiation;

prior to said positioning of said opaque pin, adjustably fixing the spacial and geometric relationship of said opaque pin to a tubular drill guide by placing both pin and drill guide in a jig usable to adjust and set the distance of the drill guide from the pin along the projected axis of the tubular drill guide;

incising the skin of the limb at the indicia positioned on the side of the limb facing the source of x-rays, and opposite the side upon which said pin is located with said incising being carried out in a direction and to a depth sufficient to permit the tubular drill guide to be directed axially through the incision and along a line between the indicia placed on the skin on opposite sides of the limb until one end of the tubular drill guide touches the fractured bone;

fixing said tubular drill guide against the fractured bone and in said incision while the drill guide axis is in substantially alignment with the axis of the fastener hole;

projecting x-ray radiation from said source through the tubular drill guide and through the fastener hole in the orthopedic nail and against the x-ray monitor to indicate on the monitor the state of alignment of the axes of the drill guide, fastener hole and opaque pin while the drill guide extends through the incision into contact with the bone; and coaxially aligning the tubular drill guide axis, the fastener hole axis and said opaque pin by adjusting the position of the drill guide as needed and as indicated by said x-ray monitor; then using the described alignment to place the fastener through the fastener hole in the orthopedic nail and into the fractured bone on opposite sides of the orthopedic nail.

5. The medical procedure of claim 4 and further characterized as comprising:

fixing the source of the x-ray radiation prior to placing the indicia on the skin so that the x-ray radiation travels in colinear alignment with the axis of said fastener hole in the orthopedic nail and will repeatedly travel in such colinear alignment when the x-ray radiation is re-developed and re-projected after having once been terminated, as long as said source is so fixed; and terminating the x-ray radiation after placing the indicia on the skin while maintaining the fixed position of the source relative to the limb, the bone and the orthopedic nail.

6. A device for use in directing drill holes transversely through a fractured long bone of a limb in directional alignment with a pair of spaced, transverse holes through an elongated orthopedic nail implaced in the medulla of the fractured long bone, said device comprising:

an elongated channel element having first and second end portions;

a first pair of indexing standards slidably secured to one end portion of said channel element for independent sliding movement in an axial direction therealong and each including drill guiding means carried thereon; and second pair of indexing standards slidably secured to the second end portion of said elongated channel element for independent sliding movement in an axial direction therealong, said second pair of indexing standards including:

a pin disc of x-ray transparent material mounted on each one of said indexing standards in said second pair of indexing standards; and an elongated x-ray opaque pin mounted in the center of each said pin discs and each having its longitudinal axis extending parallel to said channel element.

7. The device of claim 6 wherein each of said indexing standards in said first pair includes:

a foot portion spaced from said channel element;

a leg connecting said foot portion to said channel element, and spacing said foot portion from said channel element; and an elongated tubular drill guide constituting said drill guiding means mounted on said foot portion and extending parallel to said elongated channel element, said elongated tubular drill guides of said indexing standards in said first pair of indexing standards extending parallel to each other;

and wherein each of said second pair of indexing standards includes:

a second pair of foot portions spaced from said channel element;

a second pair of legs connecting said second pair of foot portions to said channel element; and each one of said elongated x-ray opaque pins having its longitudinal extending parallel to said channel element, and to said tubular drill guides on the foot portions of said first pair of indexing standards, the longitudinal axis of each one of said elongated pins being aligned with the longitudinal axes of said tubular drill guides; and said legs of said indexing standards having a length such that said foot portions will be spaced along said channel element by a distance sufficient to allow said channel element to bridge across a fractured leg in which the fractured bone is located when said elongated pins touch the skin on one side of the fractured leg in which the fractured bone is located, and said tubular drill guides touch the fractured leg in which the fractured bone is located on the opposite side thereof from the side upon which said pins are located and touch the fractured leg.

8. The device of claim 7 wherein each of said first pair of indexing standards and each of the second pair of indexing standards further includes means for releasably and independently locking the indexing standards at selected fixed positions along said elongated channel element.

9. A device for use in directing a drill hole transversely through a fractured long bone of a limb so that such drill hole is in alignment with a transverse hole through an elongated orthopedic nail implaced in the medulla of the fractured long bone, said device comprising:

an elongated guide element having a first end portion and a second end portion;

at least one first indexing standard supported on one end portion of said guide element for sliding movement in an axial direction therealong, said first indexing standard projecting normal to the longitudinal axis of said elongated guide element and comprising:

a first foot portion supported by the elongated guide element in a position spaced from said guide element; and an elongated tubular drill guide mounted on said foot portion and extending parallel to said elongated guide element;

at least one additional indexing standard supported on an opposed second end portion of said elongated guide element for sliding movement in an axial direction therealong, said additional indexing standard extending normal to said elongated guide element and comprising:

a second foot portion supported in a position spaced from said elongated guide element;

a pin disc of x-ray transparent material mounted on said foot portion of said additional indexing standard; and an elongated x-ray opaque pin mounted in the center of said pin disc and having its longitudinal axis extending parallel to said elongated guide element, and to said tubular drill guide on the first foot portion on said first indexing standard, the longitudinal axis of said elongated pin being aligned with the longitudinal axis of said tubular drill guide.

10. The device of claim 9 wherein said first indexing standard further comprises:
   means for releasably locking said first indexing standard at a selected fixed position along said elongated guide element;
   a first leg disposed between said first foot portion and said guide element for spacing said first foot portion from said guide element; and
   wherein said additional indexing standard further comprises:
      means for releasably locking the additional indexing standard at a selected fixed position along said elongated guide element; and
      a second leg disposed between said second foot portion and said guide element for spacing said second foot portion from said guide element.

11. A device for use in directing drill holes transversely through a fractured long bone of the body in alignment with a spaced, transverse hole extending through an elongated orthopedic nail placed in the medulla of the fractured long one, said device comprising:
   an elongated guide element having a first end portion and a second end portion;
   a first indexing standard movably secured to said first end portion of said guide element for movement in an axial direction therealong, said first indexing standard including:
      means for locking the first indexing standard at a selected position along the elongated guide element;
      first spacing means secured to said elongated guide element and extending normal to said elongated guide element; and
      an elongated tubular drill guide mounted on said first spacing means and extending parallel to said elongated guide element, said elongated tubular drill guide being positioned at a location spaced from said elongated guide element;
   a second indexing standard movably secured to the second end portion of said elongated guide element for movement in an axial direction therealong, said second indexing standard including;
      means for locking the second indexing standard at a fixed position along said elongated guide element;
      second spacing means secured to said elongated guide element and extending normal to said elongated guide element;
      a pin disc of x-ray transparent material mounted on said second spacing means; and
      an elongated x-ray opaque pin mounted in the center of said pin disc and having its longitudinal axis extending parallel to said guide element and in alignment with the longitudinal axis of said tubular drill guide carried on said first spacer means of said first indexing standard;
   said first and second spacing means of said first and second indexing standards each having a length such that the tubular drill guide and the pin disc and elongated x-ray opaque pin will be spaced from said guide element by a distance sufficient to allow said guide element to bridge across a leg in which the fractured bone is located when said elongated pin touches the skin on one side of the leg in which the fractured bone is located, and said tubular drill guide touches the leg in which the fractured bone is located on the opposite side thereof from the side upon which said pin is located and touches the leg.

12. A medical procedure for extending a fastening element through a transverse fastener hole in the distal end of an orthopedic nail placed within the medulla of a fractured long bone of the body to fix the location of the nail in the bone, said procedure comprising:
   projecting x-ray radiation from a source on one side of the fractured bone-containing limb linearly transversely through the fractured bone and through the fastener hole in the nail and through the limb to the side thereof opposite the source of the x-rays while maintaining the fractured limb and fractured bone immobilized and in a fixed position;
   adjusting the position of the source of x-ray radiation relative to the limb, bone and nail so that the x-ray image produced on an x-ray monitor visually indicated that the projected x-ray radiation is traveling in colinear alignment with the axis of said fastener hole in the nail;
   fixing the source of x-ray radiation so that said travel in colinear alignment is maintained as long as the x-ray radiation is developed and projected;
   placing visible indicia on the skin of the fractured limb at locations on opposite sides of the limbs where the x-ray monitor indicates x-rays traveling in said colinear alignment are entering and exiting from the fractured limb after passing through the fastener hole, and accomplishing such visible indicia placement concurrently with the projection of x-ray radiation through the fractured limb;
   terminating the x-ray radiation while maintaining the fixed position of the source relative to the limb, bone and nail;
   locating in a jig in adjustable spacial and geometric relationship to each other, (a) an x-ray opaque pin of smaller diametric size than the diameter of the fastener hole in the nail, with said pin being located in the center of an x-ray transparent disc, and (b) a tubular drill guide having its longitudinal axis aligned by the jig with said x-ray opaque pin and adjustable toward and away from said pin along said axis as both are mounted in said jig;
   incising the skin of the fractured limb at one of the visible indicia made thereon on one side of the limb to a depth sufficient to permit a tubular drill guide to be directed axially through the incision, and along a line between the visible indicia placed on the skin on opposite sides of the fractured limb until one end of the tubular drill guide touches the fractured bone;
   located said x-ray opaque pin at the precise location where said visible indicia has been marked on the opposite side of said limb from said incision;
   fixing said tubular drill guide in said incision and against the fractured bone;
   fixing the drill guide and opaque pin in their relationship to each other;
   projecting x-ray radiation from said source through the tubular drill guide and through the fastener hole to indicate the state of alignment of the axes of the tubular drill guide and the fastener hole while the drill guide extends through the incision into contact with the bone;

coaxially aligning the tubular drill guide axis and the fastener hole axis by adjusting the position of the drill guide relative to the bone as needed, and as indicated by said x-ray monitor;

drilling into the bone through the tubular drill guide so that the hole drilled in the bone is coaxially aligned with the axes of the tubular drill guide and the fastener hole; and extending a fastener through the drill hole in the bone and through the fastener hole in the orthopedic nail to fasten the nail at a fixed location in the bone.

13. A medical procedure as defined in claim 12 including the preliminary step of including said drill guide and elongated pin in a jig in which both the drill guide and the elongated pin are carried slidably on an elongated channel for movement in a direction parallel to the longitudinal axis of said elongated channel and toward and away from each other, said drill guide and elongated pin being spaced from the channel by legs which slidably support the drill guide and pin on the channel, and permit the channel to bridge across the limb containing the fractured bone when said tubular drill guide contacts the fractured bone on one side thereof and the elongated pin contacts the limb on the other side thereof.

14. A medical procedure for extending a fastening element through a transverse fastener hole in the distal end of an orthopedic nail placed within the medulla of a fractured long bone of the body to fix the location of the nail in the bone, said procedure comprising:

projecting x-ray radiation from a source on one side of the fractured bone-containing limb linearly transversely through the fractured bone and through the fastener hole in the nail and through the limb to the side thereof opposite the source of the x-rays while maintaining the limb and fractured bone immobilized in a fixed position;

adjusting the position of the source of x-ray radiation relative to the limb, bone and nail so that the x-ray image produced on an x-ray monitor visually indicates that the projected x-ray radiation is traveling in colinear alignment with the axis of said fastener hole in the nail;

fixing the source of x-ray radiation so that said travel in colinear alignment continues when the x-ray radiation is developed and projected;

placing visible indicia on the skin of the fractured limb at locations on opposite sides of the limb where the x-ray monitor indicates x-rays traveling in said colinear alignment are entering and exiting from the fractured limb, and accomplishing such visible indicia placement concurrently with the projection of x-ray radiation through the fractured limb;

terminating the x-ray radiation while maintaining the fixed position of the source relative to the limb, bone and nail;

locating in a jig in adjustable spacial and geometric relationship to each other, (a) an x-ray opaque pin of smaller diametric size than the diameter of the fastener hole in the nail, with said pin being located in the center of an x-ray transparent disc, and (b) a tubular drill guide having its longitudinal axis aligned by the jig with said x-ray opaque pin, and adjustable toward and away from said pin along said axis as both are mounted in said jig;

incising the skin of the fractured limb at one of the indicia made thereon on one side of the limb to a depth sufficient to permit a tubular drill guide to be directed axially through the incision, and along a line between the visible indicia placed on the skin on opposite sides of the fractured limb until one end of the tubular drill guide touches the fractured bone;

locating said x-ray opaque pin at the precise location where said visible indicia has been marked on the opposite side of said limb from said incision;

fixing said tubular drill guide against the fractured bone in said incision;

setting the drill guide and opaque pin in their relationship to each other;

drilling into the bone through the tubular drill guide so that the hole drilled into the bone is coaxially aligned with the axes of the tubular drill guide and fastener hole by reason of the tubular drill guide being set colinearly along a line between the visible indicia on one side of the limb, and the location of the point of the x-ray opaque pin against the visible indicia on the opposite side of the limb; and extending a fastener through the drill hole in the bone and through the fastener hole in the orthopedic nail to fasten the nail at a fixed location in the bone.

* * * * *

UNITED STATES PATENT AND TRADEMARK OFFICE
CERTIFICATE OF CORRECTION

PATENT NO. : 4,848,327
DATED : July 18, 1989
INVENTOR(S) : Kevin D. Perdue

It is certified that error appears in the above-identified patent and that said Letters Patent is hereby corrected as shown below:

In the Specification:
In Column 7, line 22, after "view" insert --which--.
In the Claims:
In Column 14, line 64, delete "determined" and insert --determining--.
In Column 19, line 29, delete "one," and insert --bone.--.

Signed and Sealed this

Twenty-second Day of May, 1990

Attest:

HARRY F. MANBECK, JR.

Attesting Officer

Commissioner of Patents and Trademarks